US007766971B2

(12) United States Patent
Gladdish, Jr. et al.

(10) Patent No.: US 7,766,971 B2
(45) Date of Patent: Aug. 3, 2010

(54) CONSTRAINED LINER LOCKING RING AND POLYETHYLENE LINER CONGRUENCY FEATURE

(75) Inventors: Bennie W. Gladdish, Jr., Gainesville, FL (US); James E. Hoyt, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 17 days.

(21) Appl. No.: 11/954,359

(22) Filed: Dec. 12, 2007

(65) Prior Publication Data

US 2008/0140215 A1      Jun. 12, 2008

Related U.S. Application Data

(60) Provisional application No. 60/869,694, filed on Dec. 12, 2006.

(51) Int. Cl.
*A61F 2/32* (2006.01)
(52) U.S. Cl. ............... 623/22.29; 623/22.21; 623/22.24
(58) Field of Classification Search ..... 623/22.17–22.2, 623/22.24, 22.25, 22.28–22.29
See application file for complete search history.

(56) References Cited

U.S. PATENT DOCUMENTS 3,226,141 A    12/1965   Sullivan, Jr.

(Continued)

FOREIGN PATENT DOCUMENTS

DE         19620750 C1  *  1/1998

EP         502815 A1   *  9/1992

(Continued)

OTHER PUBLICATIONS

English language translation of German Patent No. DE 19620750 Jan. 15, 1998.

*Primary Examiner*—David Isabella
*Assistant Examiner*—Yashita Sharma
(74) *Attorney, Agent, or Firm*—Greenberg Traurig, LLP

(57) ABSTRACT

One embodiment of the present invention relates to a prosthesis, comprising: an acetabular cup, wherein the cup has an open end and a closed end, wherein the open end of the cup is defined by a rim and wherein the rim has an outer facing surface; at least one cavity disposed in the rim, wherein the cavity extends from a first end of the cavity at the outer facing surface to a second end of the cavity that is towards the closed end of the cup, and wherein the cavity comprises an undercut at the second end of the cavity; a locking ring; and at least one tab extending from the locking ring, wherein the tab comprises a first leg and a second leg having a separation therebetween, wherein each leg has a first end and a second end, wherein the first end of each leg is at the locking ring, wherein the second end of the first leg comprises a tab protrusion, and wherein at least the second leg is resilient such that the separation between the first leg and the second leg is reduced when the second leg is deflected towards the first leg; wherein the locking ring is removably locked to the cup by placement of the locking ring adjacent the rim and insertion of the tab into the cavity such that the second leg presses against a sidewall of the cavity to initially deflect the second leg towards the first leg as the tab enters the cavity and the tab protrusion of the first leg is urged into the undercut by the second leg subsequently deflecting back away from the first leg.

11 Claims, 20 Drawing Sheets

U.S. PATENT DOCUMENTS

| | | |
|---|---|---|
| 3,608,096 A | 9/1971 | Liuh |
| 3,722,002 A | 3/1973 | Charmley |
| 3,863,273 A | 2/1975 | Avevill |
| 4,241,463 A | 12/1980 | Khovaylo |
| 4,410,295 A | 10/1983 | Ersoy et al. |
| 4,524,467 A | 6/1985 | DeCarlo, Jr. |
| 4,596,580 A | 6/1986 | Weill |
| 4,623,351 A | 11/1986 | Church |
| 4,642,123 A | 2/1987 | Noiles |
| 4,666,450 A | 5/1987 | Kenna |
| 4,676,798 A | 6/1987 | Noiles |
| 4,678,472 A | 7/1987 | Noiles |
| 4,770,658 A | 9/1988 | Geremakis |
| 4,770,659 A | 9/1988 | Kendall |
| 4,784,663 A | 11/1988 | Kenna |
| 4,798,610 A | 1/1989 | Averill et al. |
| 4,801,301 A | 1/1989 | Noiles |
| 4,871,368 A | 10/1989 | Wagner |
| 4,919,674 A | 4/1990 | Schelhas |
| 4,950,299 A | 8/1990 | Noiles |
| 4,960,427 A | 10/1990 | Noiles |
| 4,978,356 A | 12/1990 | Noiles |
| 5,019,105 A | 5/1991 | Wiley |
| 5,330,535 A | 7/1994 | Moser et al. |
| 5,387,244 A | 2/1995 | Breard |
| 5,425,778 A | 6/1995 | Zichner et al. |
| 5,458,649 A | 10/1995 | Spotorno et al. |
| 5,571,200 A | 11/1996 | Cohen et al. |
| 5,725,591 A | 3/1998 | DeCarlo, Jr. et al. |
| 5,766,260 A | 6/1998 | Whiteside |
| 5,800,555 A | 9/1998 | Gray, III |
| 5,824,108 A | 10/1998 | Huebner |
| 5,916,270 A | 6/1999 | Lipman |
| 6,093,208 A | 7/2000 | Tian |
| 6,152,961 A | 11/2000 | Ostiguy, Jr. et al. |
| 6,162,256 A | 12/2000 | Ostiguy, Jr. et al. |
| 6,368,354 B2 | 4/2002 | Burstein et al. |
| 6,416,553 B1 | 7/2002 | White et al. |
| 6,475,243 B1 | 11/2002 | Sheldon et al. |
| 6,527,808 B1 | 3/2003 | Albertorio et al. |
| 6,610,097 B2 | 8/2003 | Serbousek et al. |
| 6,966,932 B1 | 11/2005 | Schroeder |
| 7,192,449 B1 * | 3/2007 | McQueen et al. ........ 623/22.25 |
| 7,326,253 B2 | 2/2008 | Synder et al. |
| 2006/0009857 A1 | 1/2006 | Gibbs et al. |

FOREIGN PATENT DOCUMENTS

| | | |
|---|---|---|
| EP | 1 197 192 A2 | 4/2002 |
| FR | 2 765 100 | 12/1998 |
| FR | 2765100 | 12/1998 |
| FR | 2765473 | 1/1999 |
| JP | 2002017759 A * | 1/2002 |
| WO | WO 02/09615 A2 | 2/2002 |

* cited by examiner

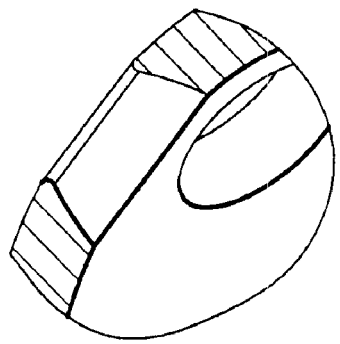
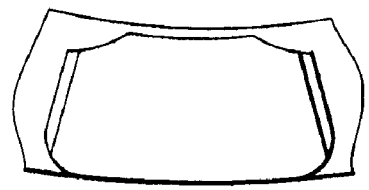
FIG.8  FIG.9
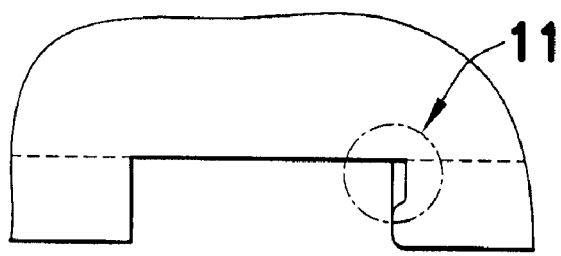
FIG.10
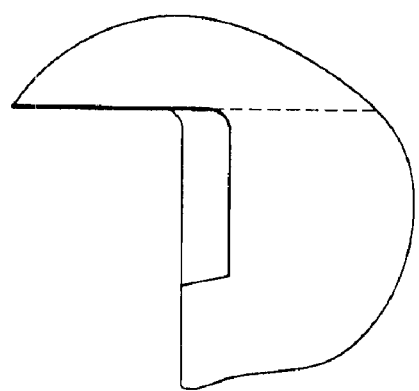
FIG.11

CONSTRAINED LINER LOCKING RING AND POLYETHYLENE LINER CONGRUENCY FEATURE

RELATED APPLICATIONS

This application claims the benefit of U.S. Provisional Application Ser. No. 60/869,694, filed Dec. 12, 2006, which is incorporated herein by reference in its entirety.

FIELD OF THE INVENTION

One embodiment of the present invention relates to a constrained liner locking ring.

Another embodiment of the present invention relates to a polyethylene liner congruency feature.

For the purposes of describing and claiming the present invention, the term "resilient" (e.g., resilient leg) is intended to refer to a component that may be deflected in a first direction in response to the application of a force and then springs back (at least partially) in a second direction that is essentially opposite to the first direction when the force is removed.

BACKGROUND OF THE INVENTION

A conventional prosthesis (e.g., for use in connection with total hip arthroplasty) includes an acetabular cup, constrained liner and locking ring.

BRIEF DESCRIPTION OF THE DRAWINGS

FIG. 8 shows detail F with reference to FIG. 3;

FIG. 9 shows detail G with reference to FIG. 2;

FIG. 10 shows detail H with reference to FIG. 1;

FIG. 11 shows detail J with reference to FIG. 10;

Of note, a feature may be identified by a reference number in a particular figure. In other figures, a similar feature may be identified by the same reference number, with the addition of an alphabetic suffix (such similar elements may differ in size and/or shape details as shown in the drawings).

Figure 1:
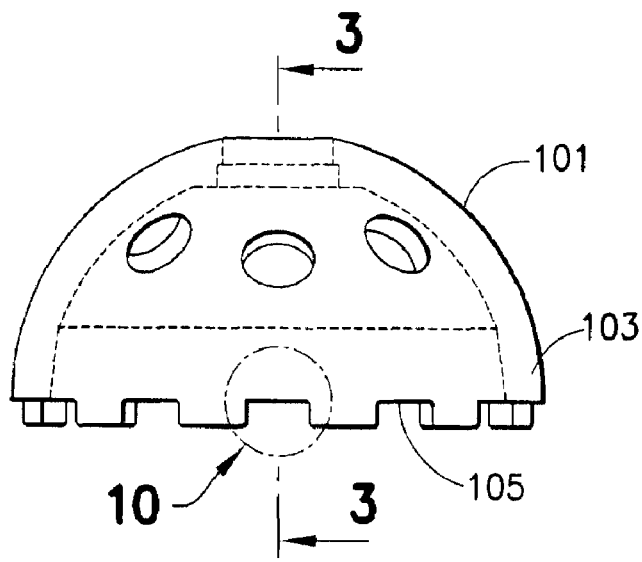
FIG. 1 is a side view of an acetabular cup (cluster hole, poly/diamond, 52 mm, group 2) according to an embodiment of the present invention.
Figure 2:
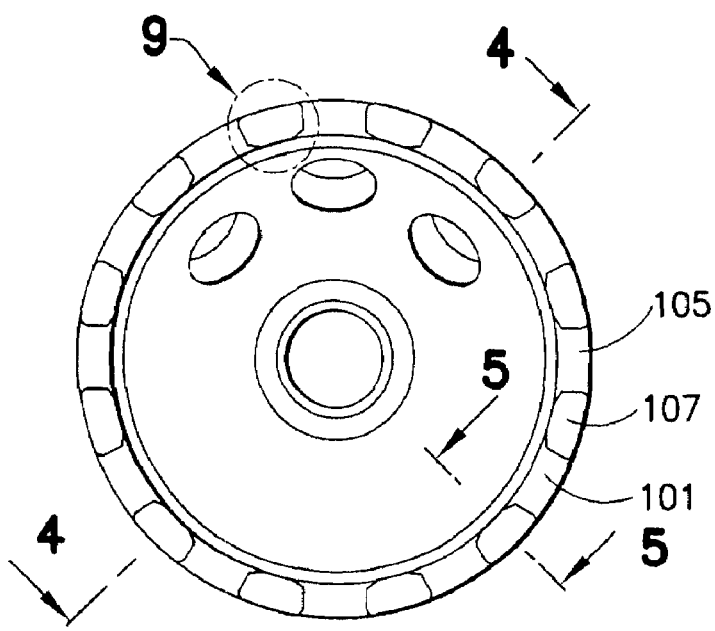
FIG. 2 is a plan view of the acetabular cup of FIG. 1.
Figure 3:
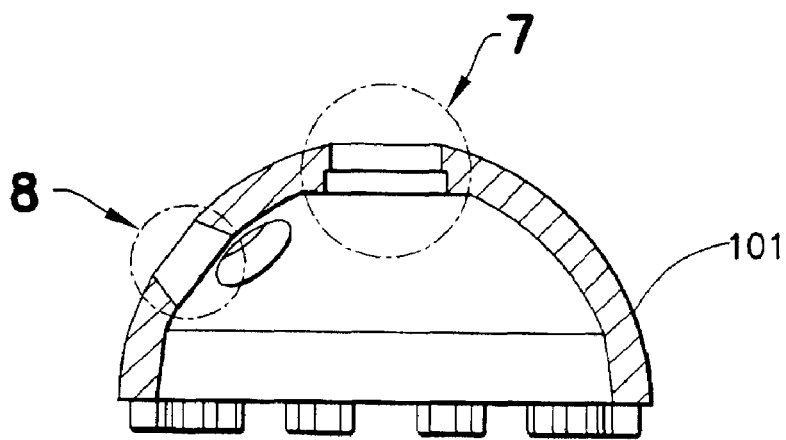
FIG. 3 is a side view (in cross-section) of the acetabular cup of FIG. 1.
Figure 4:
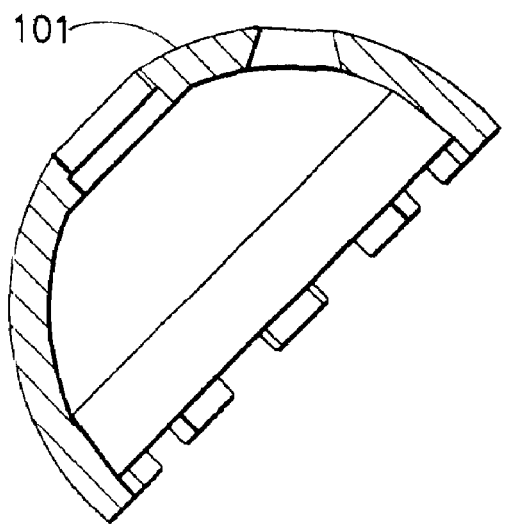
FIG. 4 is another side view (in cross-section) of the acetabular cup of FIG. 1.
Figure 5:
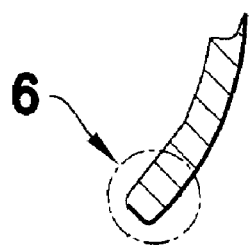
FIG. 5 shows section C-C with reference to FIG. 2.
Figure 6:
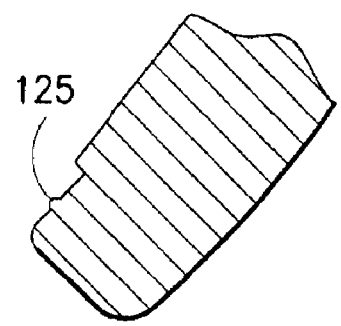
FIG. 6 shows detail D with reference to FIG. 5.
Figure 7:
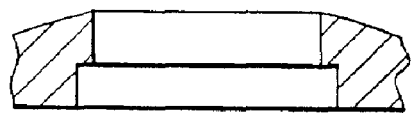
FIG. 7 shows detail E with reference to FIG. 3.
Figure 12:
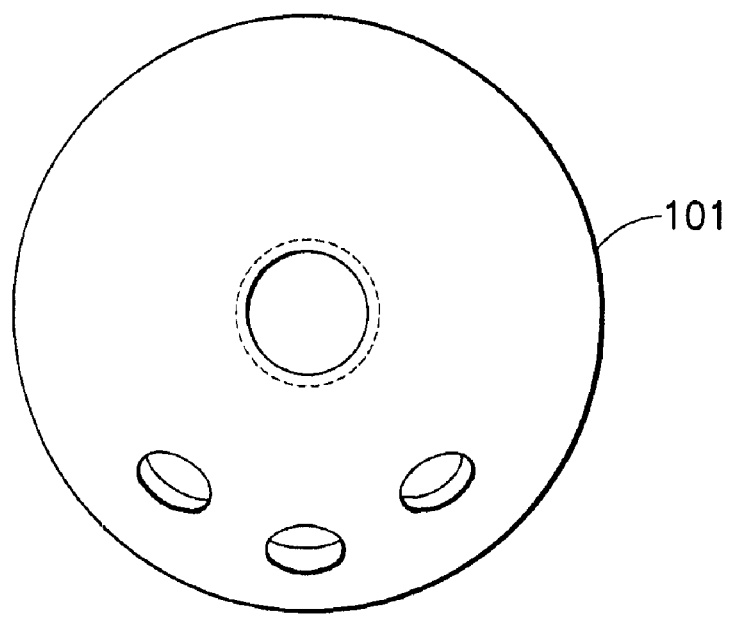
FIG. 12 is another plan view of the acetabular cup of FIG. 1.
Figure 13:
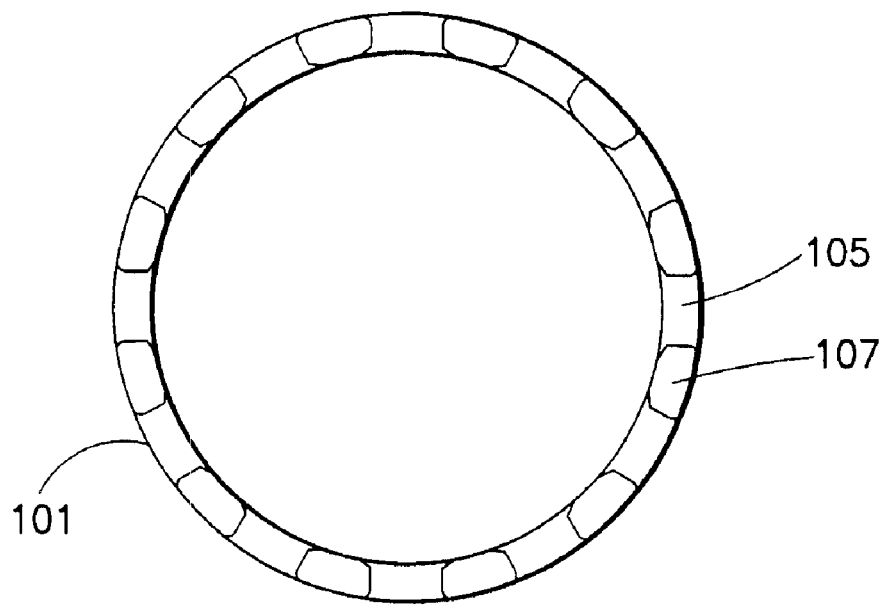
FIG. 13 is another plan view of the acetabular cup of FIG. 1.
Figure 14:
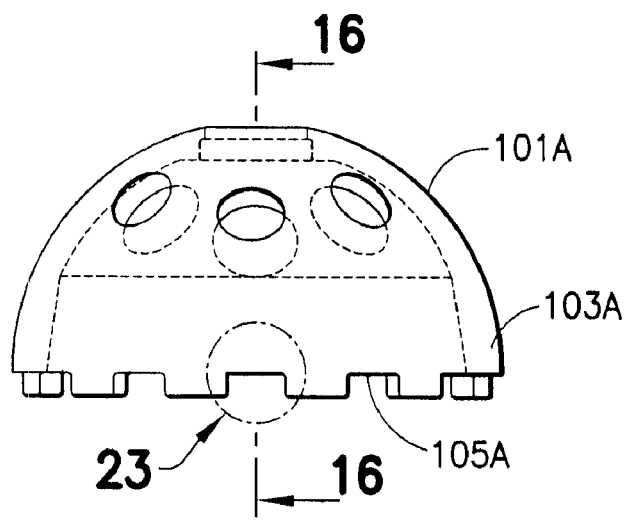
FIG. 14 is a side view of an acetabular cup (cluster hole, poly/diamond, 48 mm, group 1) according to another embodiment of the present invention.
Figure 15:
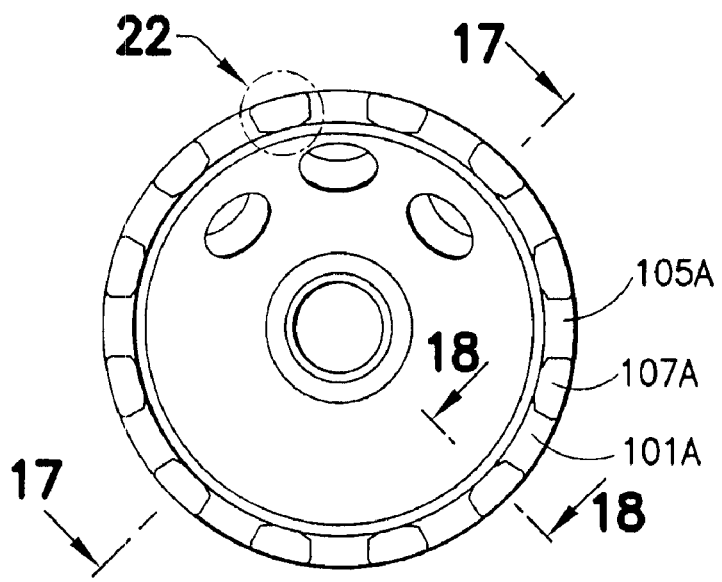
FIG. 15 is a plan view of the acetabular cup of FIG. 14.
Figure 16:
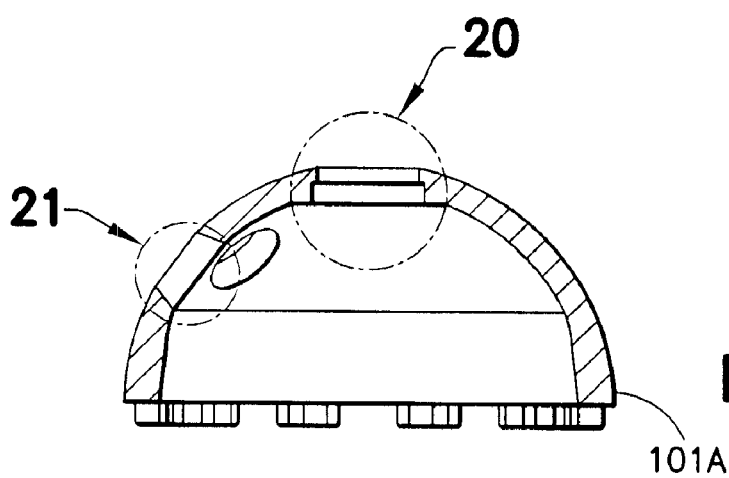
FIG. 16 is a side view (in cross-section) of the acetabular cup of FIG. 14.
Figure 17:
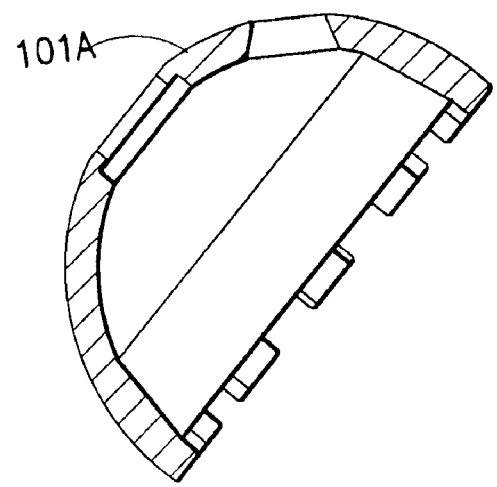
FIG. 17 is another side view (in cross-section) of the acetabular cup of FIG. 14.
Figure 18:
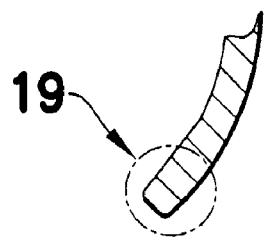
FIG. 18 shows section C-C with reference to FIG. 15.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components (and any size, material and similar details shown in the figures are, of course, intended to be illustrative and not restrictive). Therefore, specific structural and functional details disclosed herein are not to be interpreted as limiting, but merely as a representative basis for teaching one skilled in the art to variously employ the present invention.

As described herein, one embodiment of the present invention provides a constrained liner locking ring that can easily be implanted.

Further, another embodiment of the present invention provides a constrained liner locking ring in which proper mating with the acetabular cup can be confirmed.

Further still, another embodiment of the present invention provides a constrained liner locking ring which can easily be removed (e.g., to address the need for a revision). Such removal may be carried out, for example, by providing a clockwise or counter-clockwise motion to disengage a locking feature from the acetabular cup.

Further still, another embodiment of the present invention provides a constrained liner locking ring that can be used in connection with a total hip arthroplasty and that may be easily assembled and disassembled (as required).

Further still, another embodiment of the present invention provides a constrained liner locking ring that can provide a constraining feature for a polyethylene liner.

Further still, another embodiment of the present invention provides a constrained liner locking ring that can provide a constraining feature for a hard bearing surface (e.g., diamond) liner.

Further still, another embodiment of the present invention provides a constrained liner locking ring in which the geometry of each locking feature may be optimized to create the desired mechanical properties for assembly/disassembly (as required).

Further still, another embodiment of the present invention provides a constrained liner locking ring in which secure fixation of the constrained liner locking ring allows for optimization of the femoral head distraction force without the constrained liner locking ring disassociating from the acetabular cup.

Further still, another embodiment of the present invention provides a constrained liner locking ring which could be removed (e.g., should femoral head dislocation occur) by applying a clockwise or counterclockwise motion with a removal instrument. Such easy removal of the locking ring would likely not create damage to a well-fixed acetabular cup. After removal of the locking ring, the femoral head may be reduced and the locking ring re-secured to the acetabular cup.

Further, as described herein, one embodiment of the present invention provides a congruency feature (either an interrupted congruency feature or an uninterrupted congruency feature) resulting in an interference fit between a liner (e.g., a polyethylene constrained liner) and an acetabular cup (e.g., during initial implantation and subsequent thereto).

Further, in another embodiment of the present invention, the interference fit between the liner and the acetabular cup may give a tactile perception of tightness and/or minimize micro-motion at the liner/acetabular cup interface.

Further still, in one embodiment of the present invention, the interference fit may provide an improved fit between the liner at room temperature and at body temperature.

Referring now to FIGS. 1-13 and 27-34, certain details of a prosthesis according to an embodiment of the present invention will be discussed. More particularly, as seen in these Figs., an acetabular cup 101 may be provided. The cup 101 may comprise an open end and a closed end, wherein the open end of the cup 101 may be defined by a rim 103 and the rim 103 may have an outer facing surface 105. At least one cavity 107 may be disposed in the rim 103 (one cavity is called out in the Figs., but as seen, a plurality of cavities may be provided), The cavity 107 may extend from a first end of the cavity at the outer facing surface 105 to a second end of the cavity that is towards the closed end of the cup (cavity 107 may comprise an undercut at the second end of the cavity— see, e.g., FIG. 61).

Further, a locking ring 109 may be provided. At least one tab 111 (one tab is called out in the Figs., but as seen, a plurality of tabs may be provided) may extend from the locking ring 109. Tab 111 may comprise a first leg 113 and a second leg 115 having a separation therebetween. Each leg 113,115 may have a first end and a second end, wherein the first end of each leg 113,115 is at the locking ring 109, wherein the second end of the first leg 113 may comprise a tab protrusion 117, and wherein at least the second leg 115 is resilient such that the separation between the first leg 113 and the second leg 115 is reduced when the second leg 115 is deflected towards the first leg.

Figure 56:
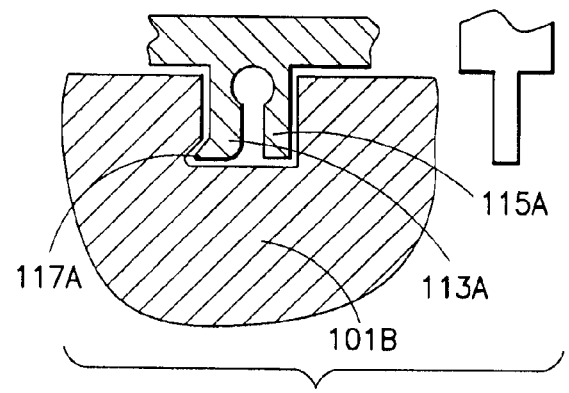
FIG. 56 is a cross-sectional view showing certain details of a tab/undercut locking mechanism for locking the locking ring of FIG. 54 to the cup of FIG. 53.

Further still, the locking ring 109 may be removably locked to the cup 101 by placement of the locking ring 109 adjacent the rim 103 and insertion of the tab 111 into the cavity 107 such that the second leg 115 presses against a sidewall of the cavity 107 to initially deflect the second leg 115 towards the first leg 113 as the tab 111 enters the cavity 107 and the tab protrusion 117 of the first leg 113 is urged into the undercut in the cavity 107 by the force of the second leg 115 subsequently deflecting back away from the first leg 113 (see, e.g., FIG. 56).

Further still, the locking ring 109 may be unlocked from the cup 101 by rotation of the locking ring 109 relative to the cup 101 such that the second leg 115 deflects towards the first leg 113 as the second leg 115 is pressed against the sidewall of the cavity 107 and the tab protrusion 117 of the first leg 113 is removed from the undercut to allow the locking ring 107 to be separated from the cup 101 (see, e.g., FIG. 56).

In one example, the first leg 113 may be resilient and the locking ring 109 may be removably locked to the cup 101 by placement of the locking ring 109 adjacent the rim 103 and insertion of the tab 111 into the cavity 107 such that the first leg 113 is pressed against the sidewall of the cavity 107 to initially deflect the first leg 113 towards the second leg 115 as the tab 111 enters the cavity 107 and the tab protrusion 117 of the first leg 113 is urged into the undercut by the force of the first leg 113 as the first leg 113 subsequently deflects back away from the second leg 115.

In another example, at least a portion of a top surface of the undercut may be angled to bias the locking ring 109 towards the rim 103 of the cup 101 when the tab protrusion 117 is urged into the undercut (see, e.g., FIG. 56).

Figure 55:
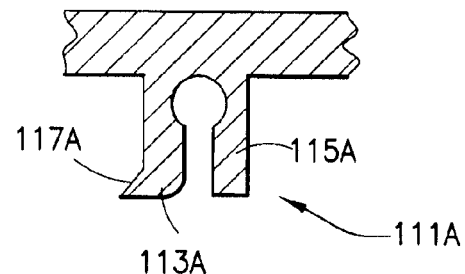
FIG. 55 shows certain details of a tab for locking the locking ring of FIG. 54 to the cup of FIG. 53.

In another example, at least a portion of a top surface of the tab protrusion 117 may be angled to bias the locking ring 109 towards the rim 103 of the cup 101 when the tab protrusion 117 is urged into the undercut (see, e.g., FIG. 55).

Figure 59:
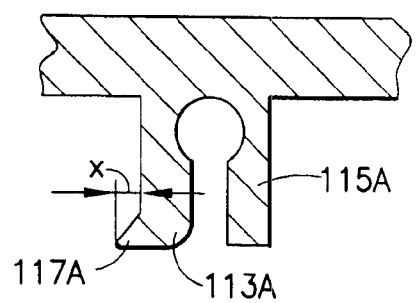
FIG. 59 shows certain details of a tab for locking the locking ring of FIG. 54 to the cup of FIG. 53.

In another example, a width of the separation between the first leg 113 and the second leg 115 may be narrower at a position at the second end of each of the first and second legs 113,115 relative to a width of the separation at a position between the second end of each of the first and second legs 113,115 and the first end of each of the first and second legs 113,115 (see, e.g., FIG. 59).

In another example, the prosthesis may further comprise a liner 119, wherein the liner 119 is disposed within the cup 101.

Figure 62:
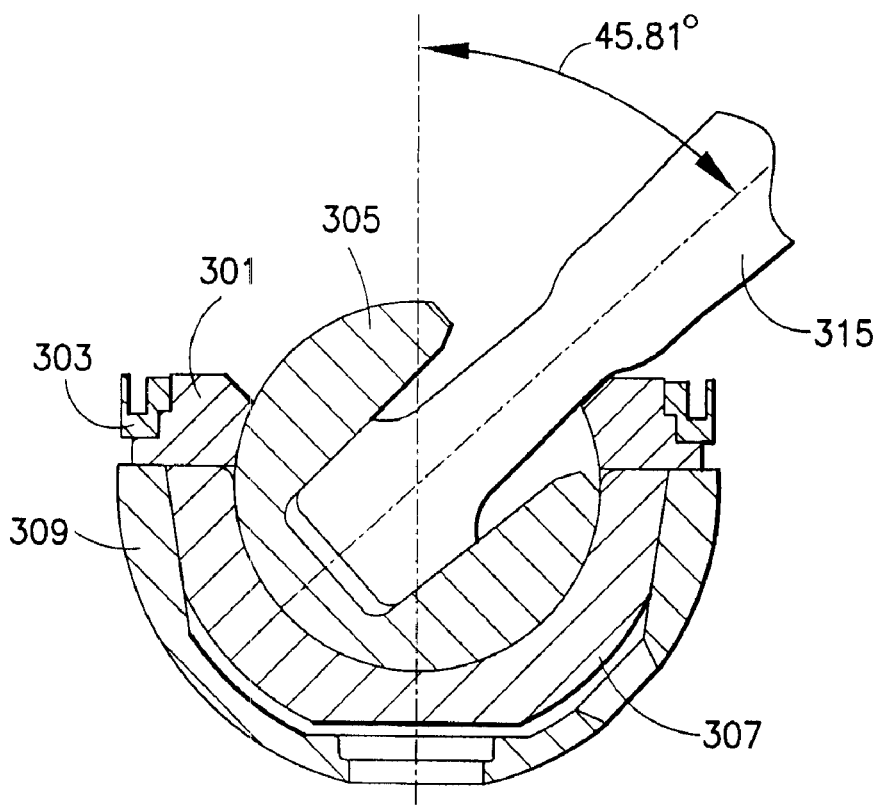
FIG. 62 shows a cross-section of a prosthesis according to another embodiment of the present invention.

In another example, the prosthesis may comprise a femoral component, wherein the femoral component comprises a ball head 305 and the ball head 305 is disposed adjacent the liner 307 when the liner 307 is disposed within the cup 309 (see, FIG. 62). In another example, the femoral component may further comprise a stem 315 attached to the ball head 305.

In another example, the ball head 305 may be held within the cup 309 by the locking ring 301/303.

In another example, the liner may comprise polyethylene.

Figure 19:
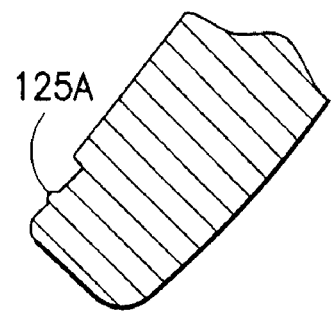
FIG. 19 shows detail D with reference to FIG. 18.
Figure 20:
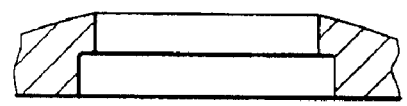
FIG. 20 shows detail E with reference to FIG. 16.
Figure 21:
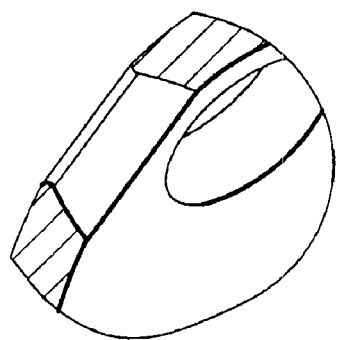
FIG. 21 shows detail F with reference to FIG. 16.
Figure 22:
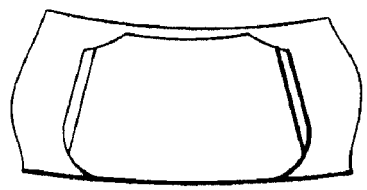
FIG. 22 shows detail G with reference to FIG. 15.
Figure 23:
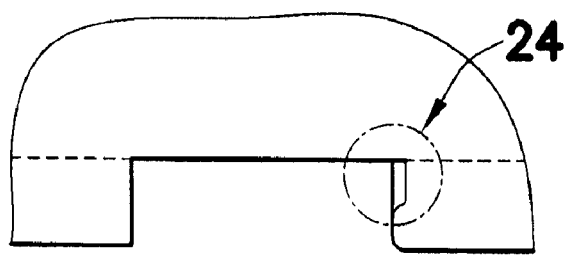
FIG. 23 shows detail H with reference to FIG. 14.
Figure 24:
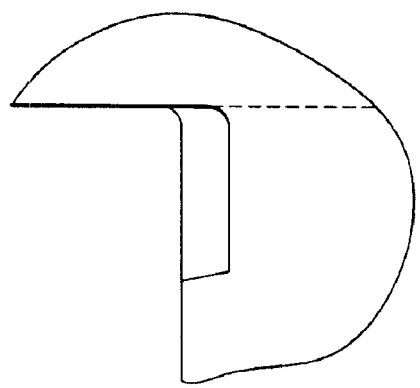
FIG. 24 shows detail J with reference to FIG. 23.
Figure 25:
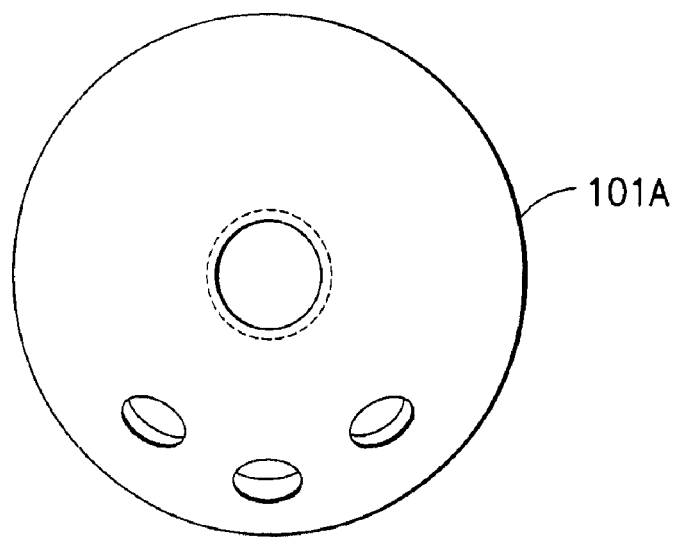
FIG. 25 is another plan view of the acetabular cup of FIG. 14.
Figure 26:
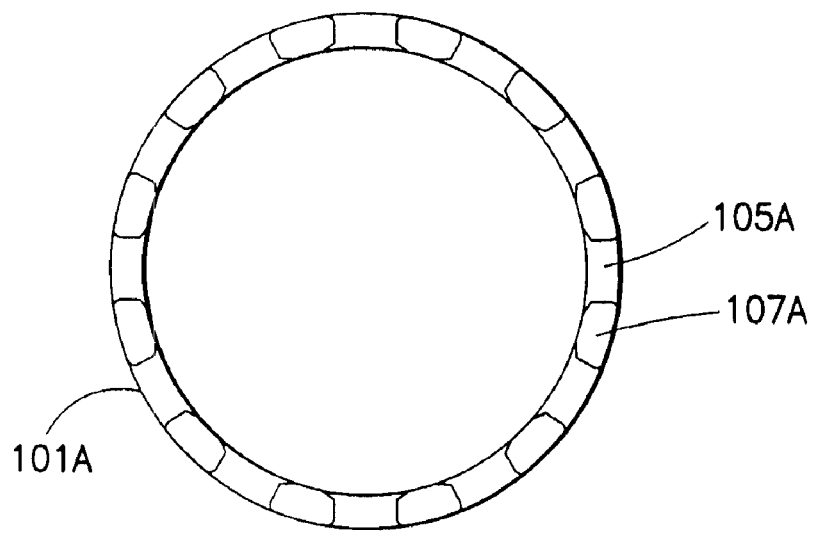
FIG. 26 is another plan view of the acetabular cup of FIG. 14.
Figure 27:
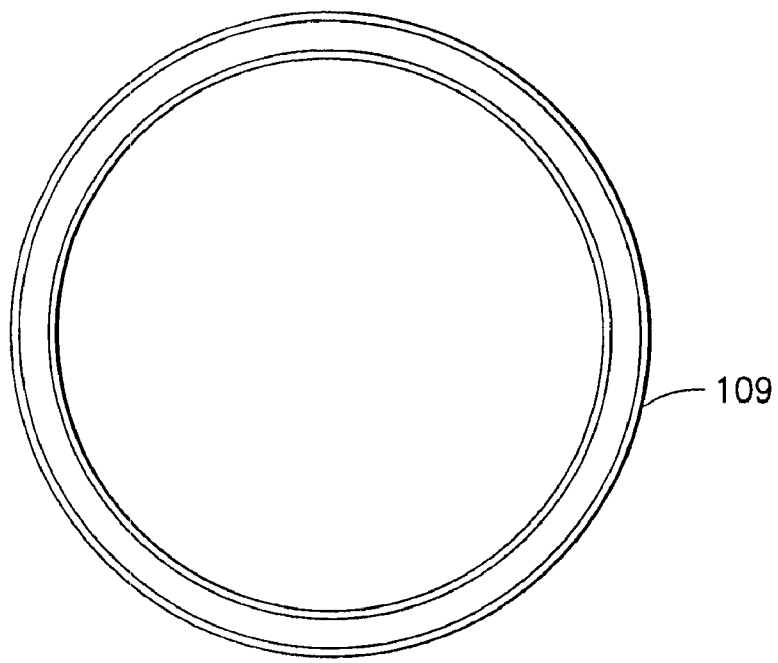
FIG. 27 is a plan view of constrained liner locking ring according to another embodiment of the present invention.
Figure 28:
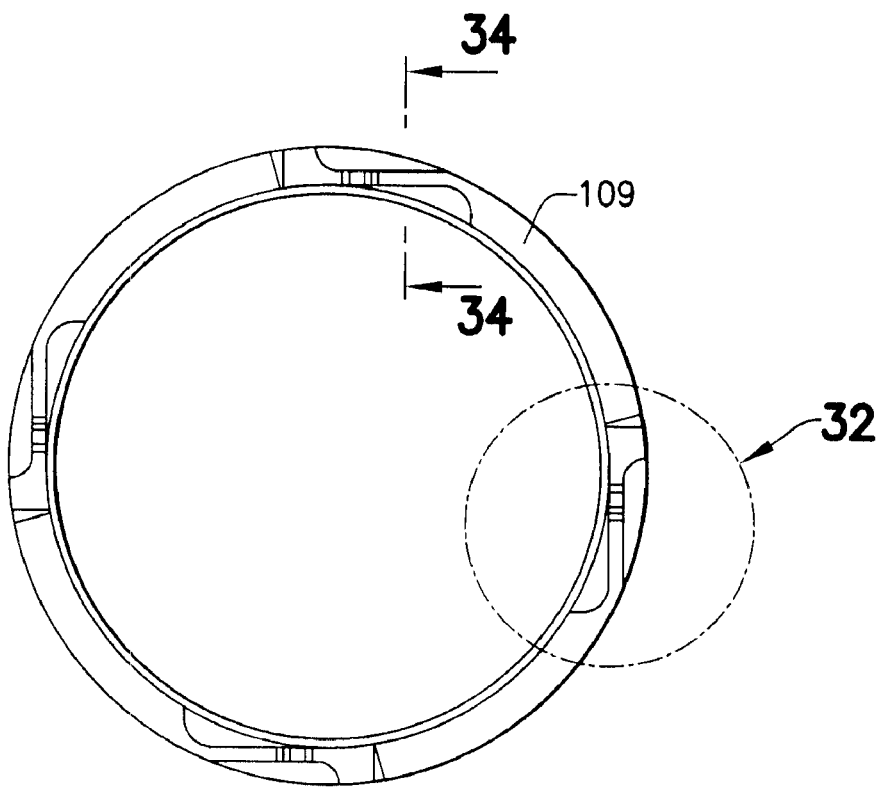
FIG. 28 is another plan view of the constrained liner locking ring of FIG. 27.
Figure 29:
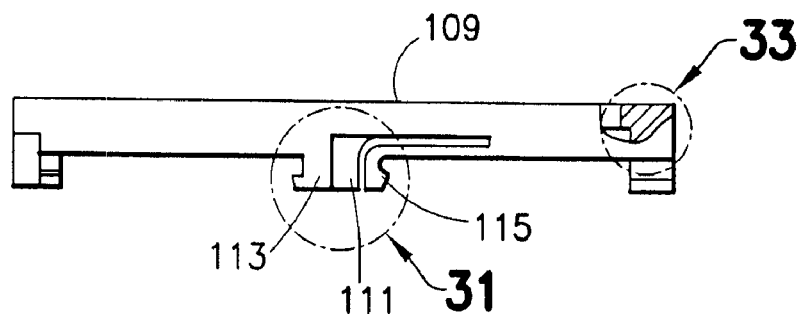
FIG. 29 is a side view of the constrained liner locking ring of FIG. 27.
Figure 30:
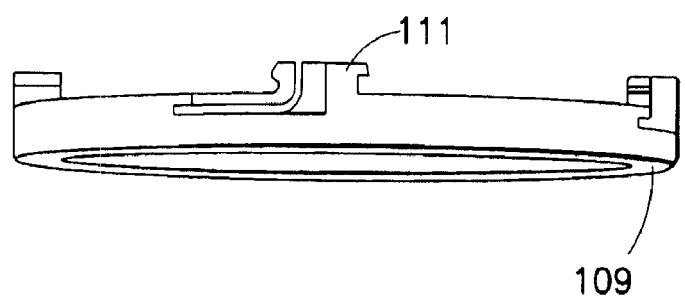
FIG. 30 is another side view of the constrained liner locking ring of FIG. 27.
Figure 31:
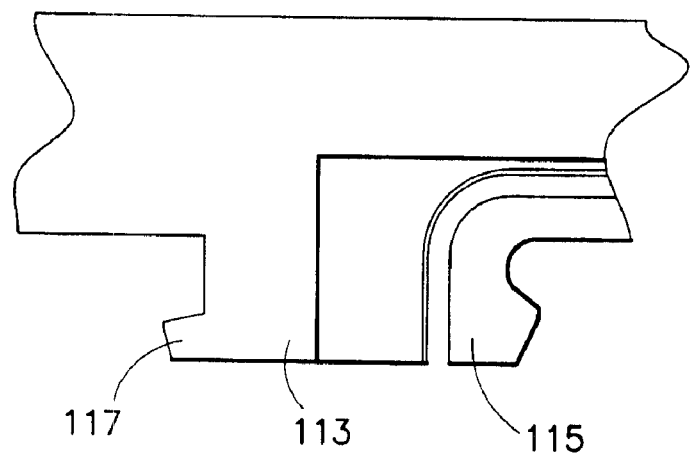
FIG. 31 shows detail B with reference to FIG. 29.
Figure 32:
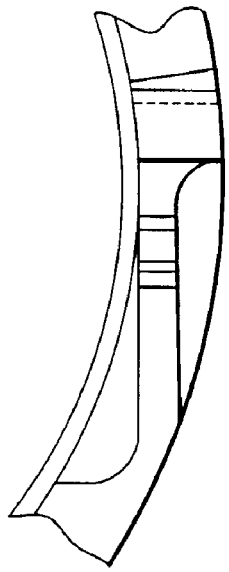
FIG. 32 shows detail A with reference to FIG. 28.
Figure 33:
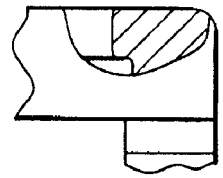
FIG. 33 shows detail E with reference to FIG. 29.
Figure 34:
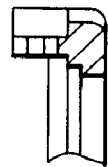
FIG. 34 shows section D-D with reference to FIG. 28.
Figure 35:
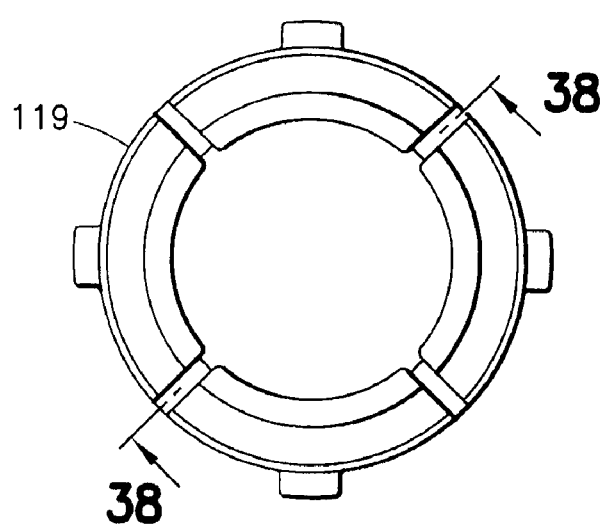
FIG. 35 is a plan view of a constrained liner (28 mm, group 1, 48/50 mm cups) according to another embodiment of the present invention.
Figure 36:
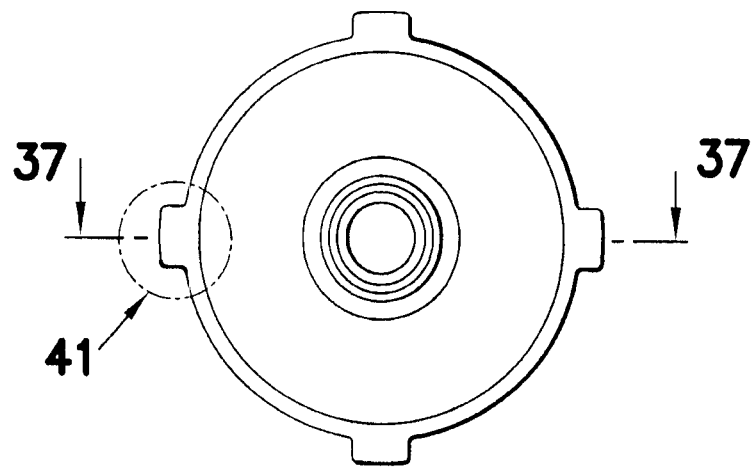
FIG. 36 is another plan view of the constrained liner of FIG. 35.
Figure 37:
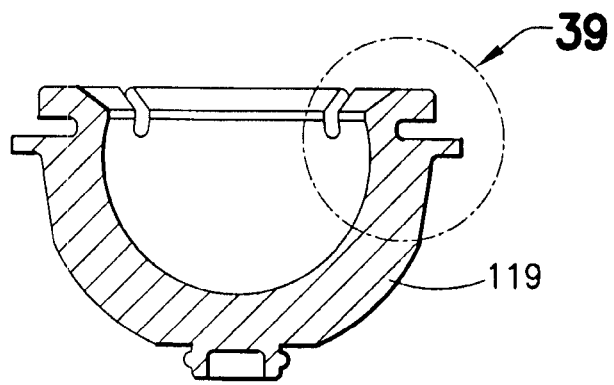
FIG. 37 is side view (in cross-section) of the constrained liner of FIG. 35.
Figure 38:
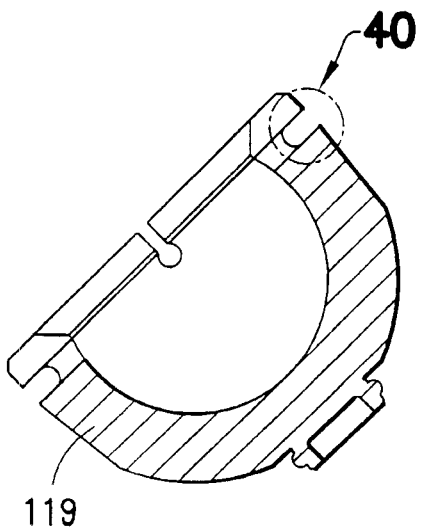
FIG. 38 shows section C-C with reference to FIG. 35.
Figure 39:
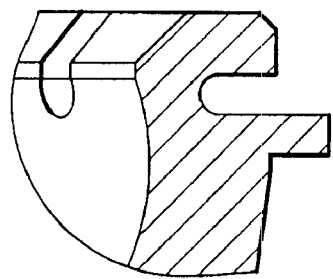
FIG. 39 shows detail E with reference to FIG. 37.
Figure 40:
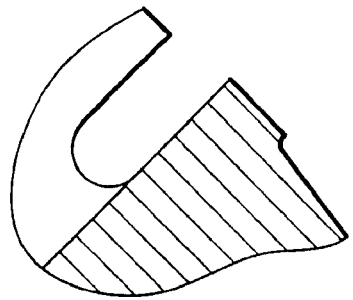
FIG. 40 shows detail F with reference to FIG. 38.
Figure 41:
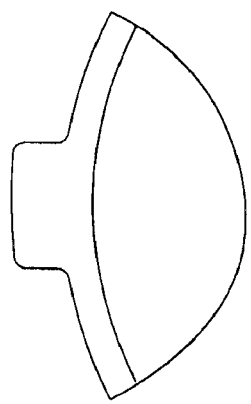
FIG. 41 shows detail B with reference to FIG. 36.
Figure 42:
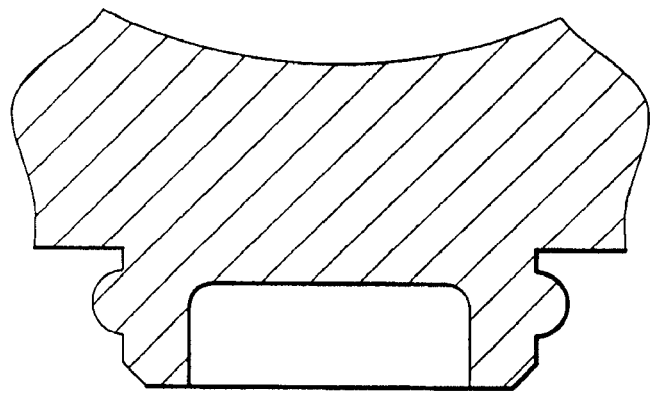
FIG. 42 shows detail D with reference to FIG. 37.
Figure 43:
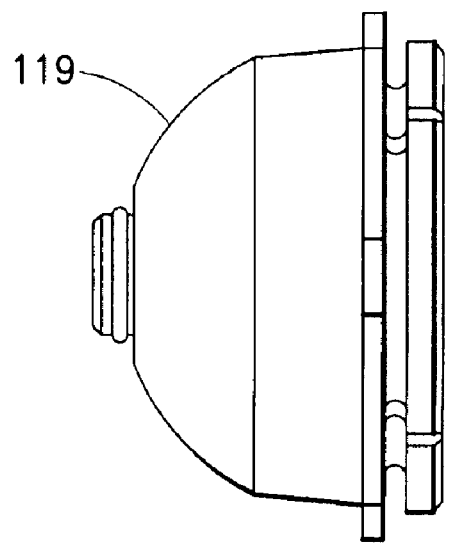
FIG. 43 shows another side view of the constrained liner of FIG. 35.
Figure 44:
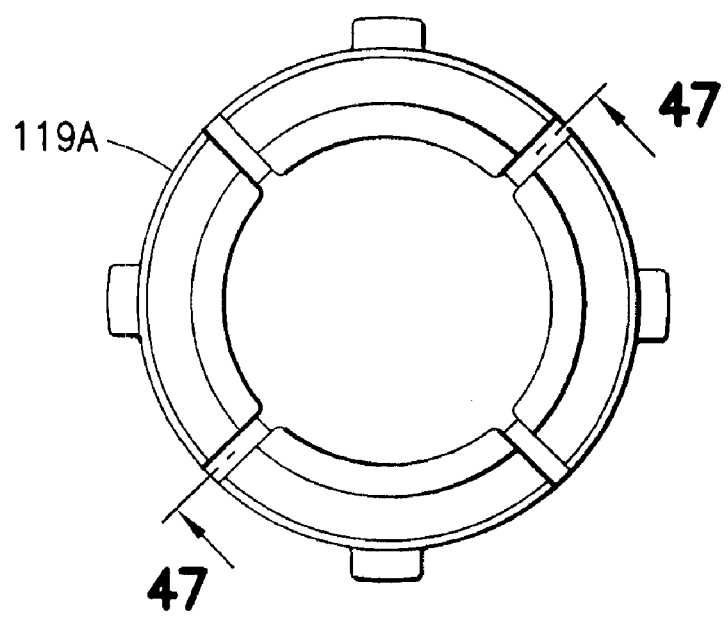
FIG. 44 is a plan view of a constrained liner (32 mm, group 2, 52/54 mm cups) according to another embodiment of the present invention.
Figure 45:
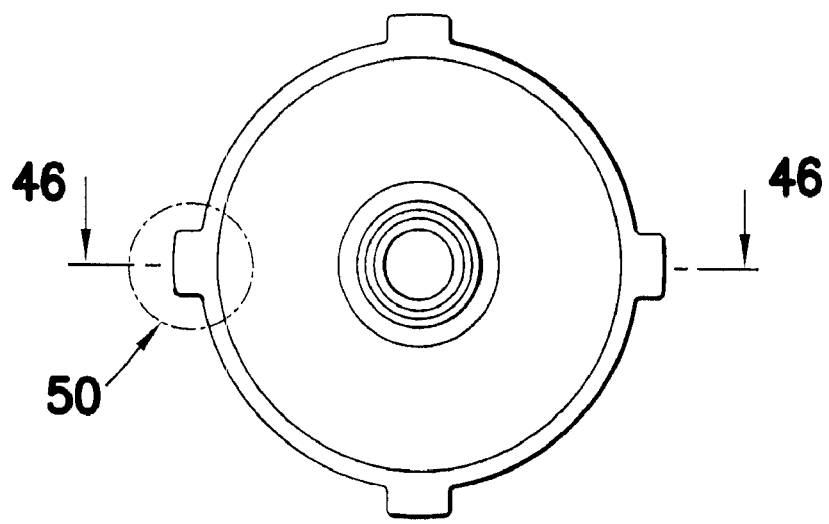
FIG. 45 is another plan view of the constrained liner of FIG. 44.
Figure 46:
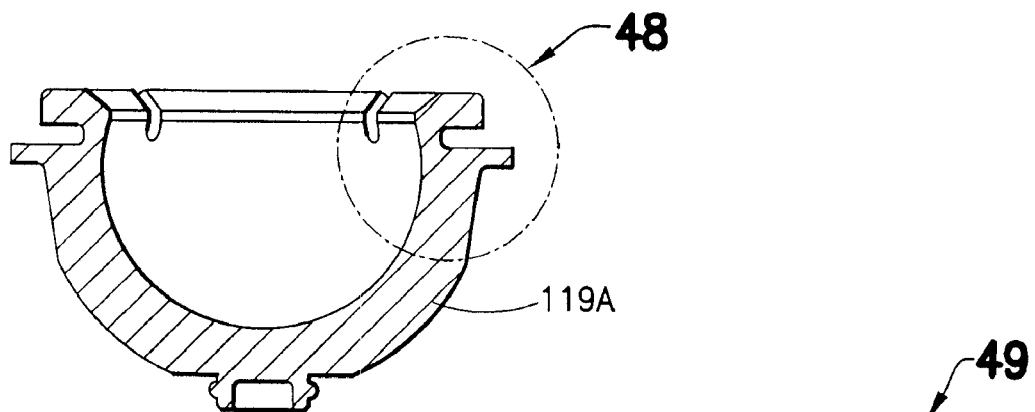
FIG. 46 is side view (in cross-section) of the constrained liner of FIG. 44.
Figure 47:
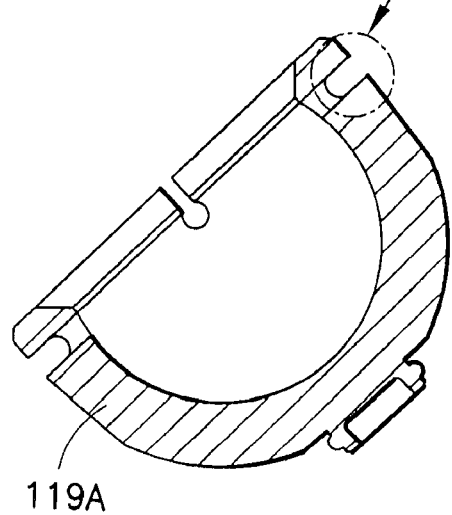
FIG. 47 shows section C-C with reference to FIG. 44.
Figure 48:
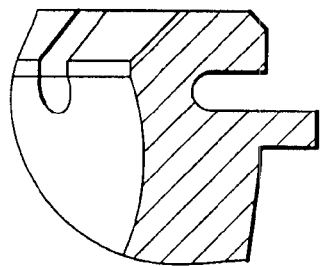
FIG. 48 shows detail E with reference to FIG. 46.
Figure 49:
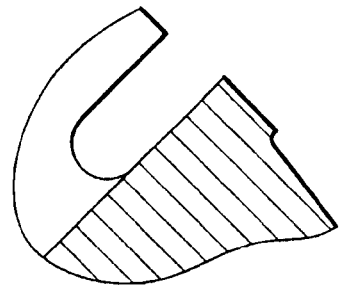
FIG. 49 shows detail F with reference to FIG. 47.
Figure 50:
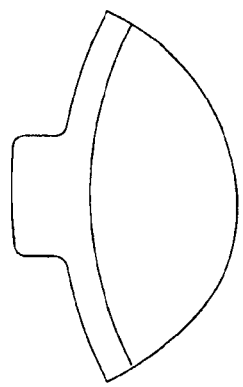
FIG. 50 shows detail B with reference to FIG. 45.
Figure 51:
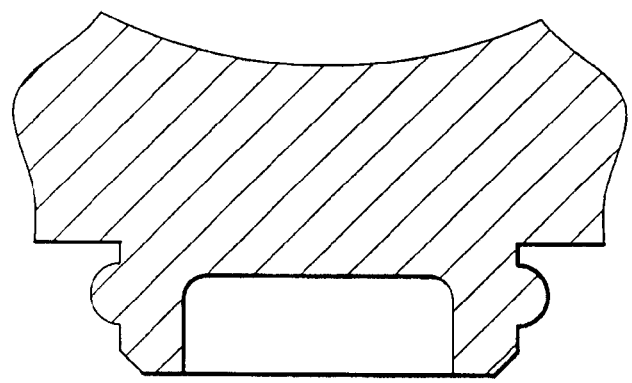
FIG. 51 shows detail D with reference to FIG. 46.
Figure 52:
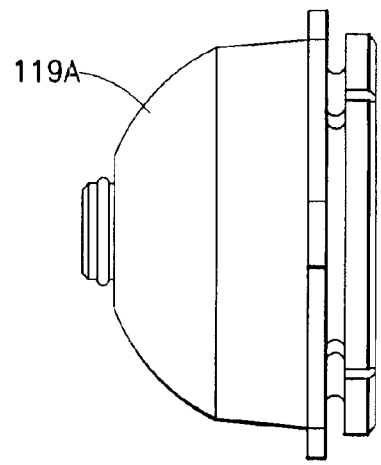
FIG. 52 shows another side view of the constrained liner FIG. 44.

In another example, cup 101 may have an inner bowl surface, an open end and a closed end; the inner bowl surface may be substantially circular adjacent the open end; and a raised feature 125 may be disposed on the inner bowl surface adjacent the open end of the cup 101 (see, e.g., FIGS. 6 and 19), wherein the raised feature 125 may be disposed around the circular perimeter of the inner bowl surface (the raised feature 125 may provide an interference fit with liner 119 disposed within the cup 101).

In another example, the raised feature may be disposed around essentially the entire circular perimeter of the inner bowl surface.

In another example, the raised feature may be interrupted at a plurality of cavities disposed in the inner bowl surface adjacent the open end.

In another embodiment, a prosthesis may be provided, comprising: an acetabular cup, wherein the cup has an open end and a closed end, wherein the open end of the cup is defined by a rim and wherein the rim has an outer facing surface; a plurality of cavities disposed in the rim, wherein each cavity extends from a first end of the cavity at the outer facing surface to a second end of the cavity that is towards the closed end of the cup, and wherein each cavity comprises an undercut at the second end of the cavity; a locking ring; and a plurality of tabs extending from the locking ring, wherein each tab comprises a first leg and a second leg having a separation therebetween, wherein each leg of each tab has a first end and a second end, wherein the first end of each leg of each tab is at the locking ring, wherein the second end of the first leg of each tab comprises a tab protrusion, and wherein at least the second leg of each tab is resilient such that the separation between the first leg and the second leg of each tab is reduced when the second leg of each tab is deflected towards the first leg of each tab; wherein the locking ring is removably locked to the cup by placement of the locking ring adjacent the rim and insertion of each tab into a respective one of the cavities such that the second leg of each tab presses against a sidewall of a respective one of the cavities to initially deflect the second leg of each tab towards the first leg of each tab as each tab enters each respective cavity and each tab protrusion of the first leg of each tab is urged into the respective undercut by the second leg of each tab subsequently deflecting back away from the first leg of each tab.

In one example, the locking ring may be unlocked from the cup by rotation of the locking ring relative to the cup such that the second leg of each tab deflects towards the first leg of each tab as the second leg of each tab is pressed against the sidewall of the respective cavity and each tab protrusion of the first leg of each tab is removed from the respective undercut to allow the locking ring to be separated from the cup.

In another example, the first leg of each tab may be resilient and the locking ring being removably locked to the cup by placement of the locking ring adjacent the rim and insertion of each tab into a respective one of the cavities may further comprise the first leg of each tab being pressed against the sidewall of the respective cavity to initially deflect the first leg of each tab towards the second leg of each tab as each tab enters the respective cavity and each tab protrusion of the first leg of each tab being urged into the respective undercut as the first leg of each tab subsequently deflects back away from the second leg of each tab.

In another example, the number of cavities may equal the integer x, the number of tabs may equal the integer x, and the integer x may be between 2 and 10, inclusive.

Figure 53:
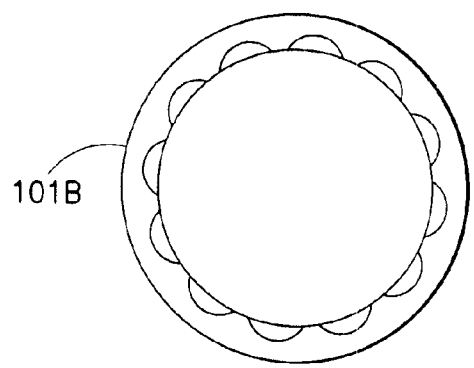
FIG. 53 is a plan view of an acetabular cup according to an embodiment of the present invention.
Figure 54:
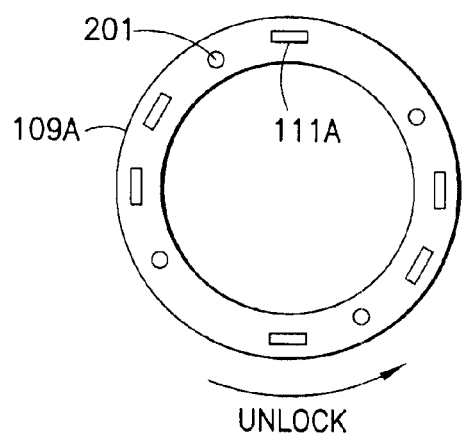
FIG. 54 is a plan view of a constrained liner locking ring according to an embodiment of the present invention.

Referring now to FIG. 53, a plan view of an acetabular cup 101B according to an embodiment of the present invention is shown. Further, FIG. 54 is a plan view of a constrained liner locking ring 109A according to an embodiment of the present invention. Further still, FIG. 55 shows certain details of a tab 111A for locking the locking ring 109A of FIG. 54 to the cup 101B of FIG. 53. Further still, FIG. 56 is a cross-sectional view showing certain details of a tab/undercut locking mechanism for locking the locking ring 109A of FIG. 54 to the cup 101B of FIG. 53. As seen in these Figs., assembly sight 201 (one assembly sight is called out in the Figs., but as seen, a plurality of assembly sights may be provided) may be used to visually confirm that locking ring 109A is fully secured against cup 101B (e.g., by looking through the assembly sight to the cup). Further, the assembly sight(s) may be used as attachment point(s) for one or more tools to assemble and/or disassemble the locking ring 109A to/from the cup 101B. Further, in this example, counter-clockwise rotation of locking ring 109A would be used to disassemble the locking ring 109A from the cup 101B (of course, the prosthesis could be configured to disassemble upon clockwise rotation of the locking ring).

Figure 57:
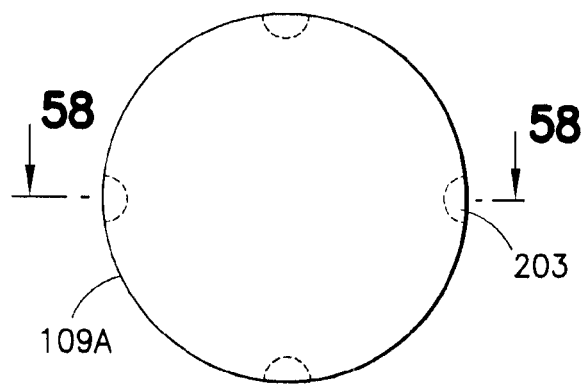
FIG. 57 is a plan view of a constrained liner locking ring according to an embodiment of the present invention.
Figure 58:
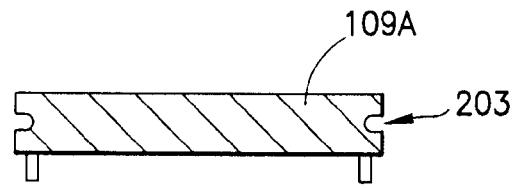
FIG. 58 shows section A-A with reference to FIG. 57.

Referring now to FIG. 57, a plan view of the constrained liner locking ring according to another embodiment of the present invention is shown. Further, FIG. 58 shows section A-A with reference to FIG. 57. As seen in these Figs. groove 203 (one groove is called out in the Figs., but a plurality of grooves may be provided) may be used as attachment point(s)

for one or more tools to assemble and/or disassemble the locking ring 109A to/from the cup 101B.

Figure 60:
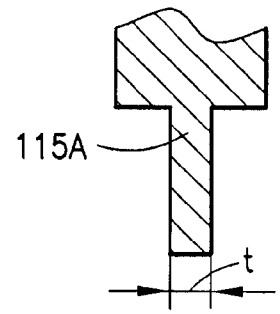
FIG. 60 shows certain details of a tab for locking the locking ring of FIG. 54 to the cup of FIG. 53.
Figure 61:
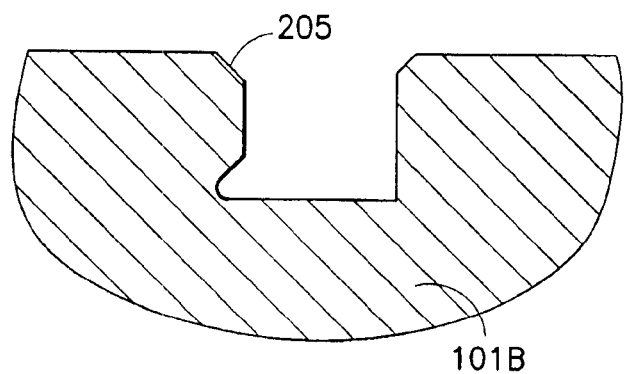
FIG. 61 shows certain details of a cavity undercut in an acetabular cup used in connection with locking the locking ring of FIG. 54 to the cup of FIG. 53.

Referring now to FIG. 59, certain details of tab 111A for locking the locking ring of FIG. 54 to the cup of FIG. 53 are shown. Further, FIG. 60 shows certain details of tab 111A for locking the locking ring of FIG. 54 to the cup of FIG. 53. Further still, FIG. 61 shows certain details of a cavity undercut in cup 101A used in connection with locking the locking ring of FIG. 54 to the cup of FIG. 53. As seen in these Figs., the length "x" of tab protrusion 117A may be optimized to obtain a desired press-fit for easy assembly and/or disassembly and/or a desired cyclic fatigue rating. Similarly, the thickness "t" of tab legs 113A,115A may be optimized to obtain a desired press-fit for easy assembly and/or disassembly and/or a desired cyclic fatigue rating (the view of FIG. 60 is 90 degrees offset from the view of FIG. 59). Further, as seen in FIG. 59, the separation between legs 113A,115A may include what is referred to a as "key" to help reduce stress riser and allow for deflection of leg 113A and/or leg 115A during assembly and/or disassembly (the "key" may be optimized to obtain a desired press-fit for easy assembly and/or disassembly and/or a desired cyclic fatigue rating). Of course, "x", "t" and the size and geometry of the "key" may be optimized individually or in relation to one another. Finally, as seen in FIG. 61, cavity 107B may include lead in chamfer 205 (to aid in assembly).

Figure 63:
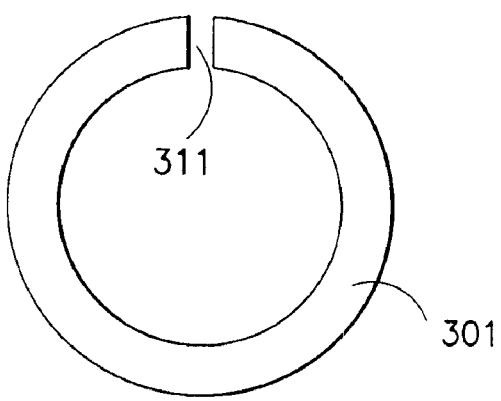
FIG. 63 shows a plan view of an example locking ring of the type used in connection with the prosthesis of FIG. 62.
Figure 64:
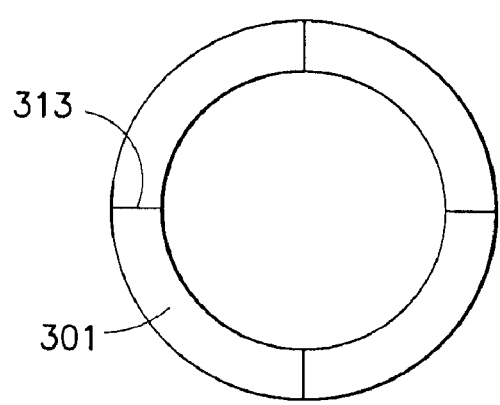
FIG. 64 shows another plan view of an example locking ring of the type used in connection with the prosthesis of FIG. 62.

Referring now to FIG. 62, a cross-section of a prosthesis according to another embodiment of the present invention is shown. Further, FIG. 63 shows a plan view of an example locking ring of the type used in connection with the prosthesis of FIG. 62. Further still, FIG. 64 shows another plan view of an example locking ring of the type used in connection with the prosthesis of FIG. 62. As seen in these Figs., the use of a polyethylene or hard bearing constraining ring 301 and a locking ring 303 may provide a mechanism to constrain a hard bearing surface (e.g., ball 305 and hard bearing surface liner 307) within acetabular cup 309 for total hip arthroplasty. The polyethylene or hard bearing constraining ring 301 may be placed on the rim of the hard bearing surface liner 307 (e.g., diamond, ceramic, metal) to prevent distraction of the ball 305 from the cup 309. In one example, the polyethylene or hard bearing constraining ring 301 may have a single slot 311 to facilitate implantation over the ball (see FIG. 63). In another example, the polyethylene or hard bearing constraining ring 301 may have multiple slots 313 (one slot is called out in the Figs., but as seen, a plurality of slot may be provided), which may be determined by a desired assembly force (see FIG. 64). In one specific example, there may be 2, 4 or 6 multiple partial slots. Further, the prosthesis may comprise stem 315.

Figure 65:
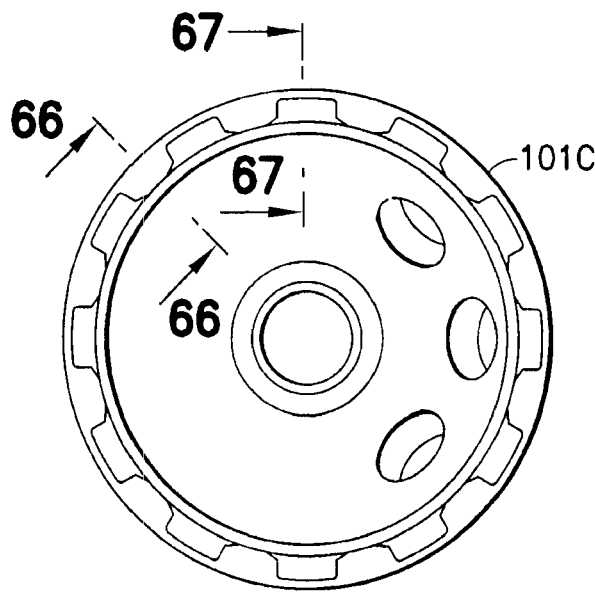
FIG. 65 is a plan view of an acetabular cup according to an embodiment of the present invention.
Figure 66:
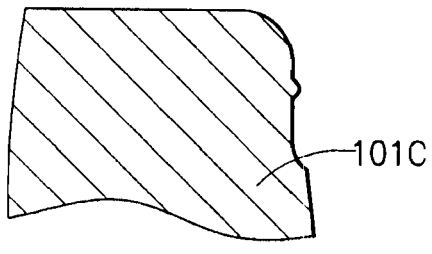
FIG. 66 shows a cross-section of an example interference fit feature of the acetabular cup of FIG. 65.
Figure 67:
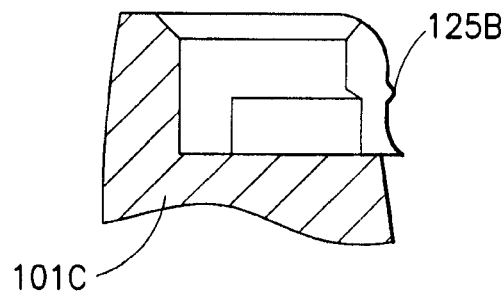
FIG. 67 shows another cross-section of an example interference fit feature of the acetabular cup of FIG. 65.

Referring now to FIG. 65, a plan view of an acetabular cup according to an embodiment of the present invention is shown. Further, FIG. 66 shows a cross-section of an example interference fit feature of the acetabular cup of FIG. 65. Further still, FIG. 67 shows another cross-section of an example interference fit feature of the acetabular cup of FIG. 66. As seen in these Figs., to improve congruency (fit) of a polyethylene liner at room temperature, a raised feature 125B is provided. In one example, this raised feature 125B is interrupted by the anti-rotation notches in the cup 101C.

The raised feature ("blip" located just below the face of the acetabular cup at the opening of the acetabular cup) creates interference between the acetabular cup and the liner. In this example, the liner has a continuous diameter slightly larger than the diameter created by the "blip" to create an interference fit between the two parts. In this example, there are twelve "blips" located inside of the acetabular crown cup due to the interruptions created for the anti-rotation feature (any desired number other than 12 may, of course, be used). In one example, the length of the "blip" feature may be held constant for all cup diameters so that essentially the same insertion force range is experienced during implantations. The insertion force can be optimized for a particular application by increasing or decreasing the "blip" length and/or the amount of interference between the "blip" and the liner.

Of note, the raised feature discussed above may provide a surgeon with the perception that a polyethylene liner for an acetabular cup is tight or fully congruent at room temperature (the typical reality is that the polyethylene liner will expand/grow to produce a tight fit between the polyethylene liner and the metal acetabular cup once the system has stabilized to body temperature (about 37° C.), provided that the initial fit is reasonably tight).

Of further note, a highly congruent polyethylene liner against a metal support (e.g., acetabular cup) may be key to evenly distributing stresses developed in the polyethylene liner from normal joint forces. If two mating parts (one polyethylene and the other metal) are not congruent, the polyethylene will cold flow to find an equilibrium state. The cold flow event creates changes in the liner geometry to compensate for differences in the mating geometries.

Figure 68:
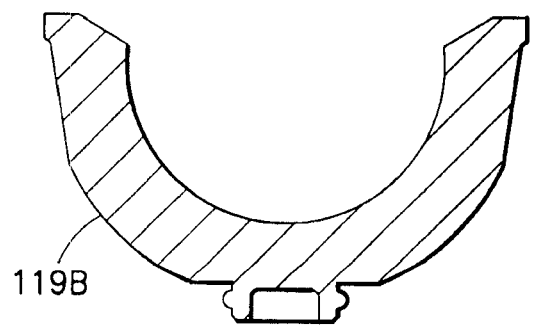
FIG. 68 shows a cross-section of an example interference fit feature of a polyethylene liner according to an embodiment of the present invention.

Referring now to FIG. 68, this shows a cross-section of an example interference fit feature of a polyethylene liner. More particularly, as seen in this FIG., constrained liner 119B may include a depression or a raised portion ("congruency feature") for providing an interference fit with an acetabular cup.

While a number of embodiments of the present invention have been described, it is understood that these embodiments are illustrative only, and not restrictive, and that many modifications may become apparent to those of ordinary skill in the art. For example, any element described herein may be provided in any desired size (e.g., any element described herein may be provided in any desired custom size or any element described herein may be provided in any desired size selected from a "family" of sizes, such as small, medium, large). Further, one or more of the components may be made from any of the following materials: (a) any biocompatible material (which biocompatible material may be treated to permit surface bone ingrowth or prohibit surface bone ingrowth—depending upon the desire of the surgeon); (b) a plastic; (c) a fiber; (d) a polymer; (e) a metal (a pure metal such as titanium and/or an alloy such as Ti—Al—Nb, Ti-6Al-4V, stainless steel); (f) any combination thereof. Further still, any metal construct may be a machined metal construct. Further still, any number of protrusions (e.g., such as for initial fixation by forming a bond with cement and/or such as for supplemental fixation by forming a bond with cement) may be utilized with a given prosthesis. Further still, any number of female features that increase the cement mantle may be utilized with a given prosthesis. Further still, any number of male features that could dig into the bone so that initial/supplemental fixation can be improved may be utilized with a given prosthesis. Further still, any number of bone screws (e.g., such as for initial fixation and/or such as for supplemental fixation) may be utilized with a given prosthesis. Further still, any steps described herein may be carried out in any desired order (and any additional steps may be added as desired and/or any steps may be deleted as desired).

What is claimed is:

1. A prosthesis, comprising:
   an acetabular cup, wherein the cup has an open end and a closed end, wherein the open end of the cup is defined by a rim and wherein the rim has an outer facing surface;

at least one cavity disposed in the rim, wherein the cavity extends from a first end of the cavity at the outer facing surface to a second end of the cavity that is towards the closed end of the cup, and wherein the cavity comprises an undercut at the second end of the cavity;

a liner, wherein the liner is disposed within the cup;

a femoral component, wherein the femoral component comprises a ball head and the ball head is disposed adjacent the liner when the liner is disposed within the cup;

a separate locking ring that is removably locked to the cup; and at least one tab extending from the locking ring, wherein the tab comprises a first leg and a second leg having a separation therebetween, wherein each leg has a first end and a second end, wherein the first end of each leg is at the locking ring, wherein the second end of the first leg comprises a tab protrusion, and wherein at least the second leg is resilient such that the separation between the first leg and the second leg is reduced when the second leg is deflected towards the first leg;

wherein the locking ring is removably locked to the cup by placement of the locking ring adjacent the rim and insertion of the tab into the cavity such that the second leg presses against a sidewall of the cavity to initially deflect the second leg towards the first leg as the tab enters the cavity and the tab protrusion of the first leg is urged into the undercut by the second leg subsequently deflecting back away from the first leg.

2. The prosthesis of claim 1, wherein the locking ring is unlocked from the cup by rotation of the locking ring relative to the cup such that the second leg deflects towards the first leg as the second leg is pressed against the sidewall of the cavity and the tab protrusion of the first leg is removed from the undercut to allow the locking ring to be separated from the cup.

3. The prosthesis of claim 1, wherein:

the first leg is resilient; and the locking ring being removably locked to the cup by placement of the locking ring adjacent the rim and insertion of the tab into the cavity further comprises the first leg being pressed against the sidewall of the cavity to initially deflect the first leg towards the second leg as the tab enters the cavity and the tab protrusion of the first leg being urged into the undercut as the first leg subsequently deflects back away from the second leg.

4. The prosthesis of claim 1, wherein the ball is held within the cup by the locking ring.

5. The prosthesis of claim 1, wherein the liner comprises polyethylene.

6. A prosthesis, comprising:

an acetabular cup, wherein the cup has an open end and a closed end, wherein the open end of the cup is defined by a rim and wherein the rim has an outer facing surface;

a plurality of cavities disposed in the rim, wherein each cavity extends from a first end of the cavity at the outer facing surface to a second end of the cavity that is towards the closed end of the cup, and wherein each cavity comprises an undercut at the second end of the cavity;

a liner, wherein the liner is disposed within the cup;

a femoral component, wherein the femoral component comprises a ball head and the ball head is disposed adjacent the liner when the liner is disposed within the cup;

a separate locking ring that is removably locked to the cup; and a plurality of tabs extending from the locking ring, wherein each tab comprises a first leg and a second leg having a separation therebetween, wherein each leg of each tab has a first end and a second end, wherein the first end of each leg of each tab is at the locking ring, wherein the second end of the first leg of each tab comprises a tab protrusion, and wherein at least the second leg of each tab is resilient such that the separation between the first leg and the second leg of each tab is reduced when the second leg of each tab is deflected towards the first leg of each tab;

wherein the locking ring is removably locked to the cup by placement of the locking ring adjacent the rim and insertion of each tab into a respective one of the cavities such that the second leg of each tab presses against a sidewall of a respective one of the cavities to initially deflect the second leg of each tab towards the first leg of each tab as each tab enters each respective cavity and each tab protrusion of the first leg of each tab is urged into the respective undercut by the second leg of each tab subsequently deflecting back away from the first leg of each tab.

7. The prosthesis of claim 6, wherein the locking ring is unlocked from the cup by rotation of the locking ring relative to the cup such that the second leg of each tab deflects towards the first leg of each tab as the second leg of each tab is pressed against the sidewall of the respective cavity and each tab protrusion of the first leg of each tab is removed from the respective undercut to allow the locking ring to be separated from the cup.

8. The prosthesis of claim 6, wherein:

the first leg of each tab is resilient; and the locking ring being removably locked to the cup by placement of the locking ring adjacent the rim and insertion of each tab into a respective one of the cavities further comprises the first leg of each tab being pressed against the sidewall of the respective cavity to initially deflect the first leg of each tab towards the second leg of each tab as each tab enters the respective cavity and each tab protrusion of the first leg of each tab being urged into the respective undercut as the first leg of each tab subsequently deflects back away from the second leg of each tab.

9. The prosthesis of claim 6, wherein the number of cavities equals the integer x, the number of tabs equals the integer x, and the integer x is between 2 and 10, inclusive.

10. The prosthesis of claim 1, whereint he locking ring holds the ball head of the femoral component within the cup.

11. The prosthesis of claim 1, further comprising a constraining ring, wherein the constraining ring and the locking ring hold the ball head of the femoral component and the liner within the cup.

* * * * *

UNITED STATES PATENT AND TRADEMARK OFFICE
CERTIFICATE OF CORRECTION

| | |
|---|---|
| PATENT NO. | : 7,766,971 B2 |
| APPLICATION NO. | : 11/954359 |
| DATED | : August 3, 2010 |
| INVENTOR(S) | : Bennie W. Gladdish, Jr. et al. |

Page 1 of 1

It is certified that error appears in the above-identified patent and that said Letters Patent is hereby corrected as shown below:

Col. 10, Ln. 54, Delete "whereint he"
                Insert --wherein the--

Signed and Sealed this

Thirtieth Day of November, 2010

David J. Kappos
*Director of the United States Patent and Trademark Office*